United States Patent [19]
Miller

[11] Patent Number: 5,839,942
[45] Date of Patent: Nov. 24, 1998

[54] POST-PARTUM BREAST ENGORGEMENT BRA

[75] Inventor: Michael Miller, Boca Raton, Fla.

[73] Assignee: International Medical Supplies, Inc., Reno, Nev.

[21] Appl. No.: 683,466

[22] Filed: Jul. 18, 1996

Related U.S. Application Data

[63] Continuation of Ser. No. 361,834, Dec. 22, 1994.

[51] Int. Cl.⁶ .................................................. A41C 3/00
[52] U.S. Cl. .................................. 450/58; 2/73; 450/93; 450/32; 450/89
[58] Field of Search .................................. 2/73, 105, 106, 2/114, 113, 115; 450/30, 31, 32, 53, 54, 55, 56, 57, 70, 19, 20, 21, 74, 75, 76, 77, 79, 80, 82, 83, 84, 85, 93, 89

[56] References Cited

U.S. PATENT DOCUMENTS

| | | | |
|---|---|---|---|
| 669,770 | 3/1901 | Steppacher et al. | 2/106 |
| 1,014,317 | 1/1912 | Merkel | 2/106 |
| 1,043,505 | 11/1912 | Brooker | 2/106 |
| 3,173,420 | 3/1965 | Mazzoni et al. | 450/54 |
| 3,421,514 | 1/1969 | Friedlander | 450/86 |
| 3,968,803 | 7/1976 | Hyman | 450/58 |
| 5,032,104 | 7/1991 | Rainville | 450/58 |
| 5,098,331 | 3/1992 | Corrado | 450/58 |
| 5,180,326 | 1/1993 | Williams | 450/58 |
| 5,190,033 | 3/1993 | Johnson | 607/108 |
| 5,427,563 | 6/1995 | Manning | 450/57 |

Primary Examiner—Jeanette E. Chapman
Attorney, Agent, or Firm—Cushman Darby & Cushman Intellectual Property Group of Pillsbury Madison & Sutro LLP

[57] ABSTRACT

The present invention concerns a bra for the support and compression of the breasts of a woman suffering from post-partum breast engorgement, enlargement, or other conditions of the breasts. The bra includes a front panel connected to a back panel forming a garment. The garment is separable and includes connectors at the separation. The connectors are selectively connectable to provide an adjustable girth size of the garment. Variation in the girth size provides adjustable compression. The present invention also concerns warm or cold compresses in combination with a bra for the support and compression of breasts.

10 Claims, 6 Drawing Sheets

POST-PARTUM BREAST ENGORGEMENT BRA

This application is a continuation of Ser. No. 08/361,834, filed Dec. 22, 1994.

BACKGROUND OF THE INVENTION

1. Field of the Invention

The present invention relates to bras and, more particularly, to a bra that compresses and supports the breasts of a woman having post-partum breast engorgement, enlargement, or other conditions of the breasts.

2. Description of the Related Art

One of the unavoidable consequences of pregnancy and child birth is post-partum breast engorgement and enlargement. Women suffering from such conditions experience pain and discomfort of the breasts. The pain is acute particularly for women that choose not to nurse. Presently, the options available to women and their doctors for treatment are limited.

Lactation suppressants prevent engorgement and, consequently, concomitant discomfort. The lactation suppressant bromocriptine mesylate, however, marketed under the trade name Parlodel, was taken off the market by the manufacturer. It had been criticized by the Food and Drug Administration in light of the correlation between the drug and seizures, strokes, and heart attacks.

Without safe, available pharmacological treatments, doctors presently recommend ice packs or warm baths. These treatments, however, are limited practically. Baths and ice packs may be unavailable or inappropriate for all situations.

SUMMARY OF THE INVENTION

An object of the present invention is to provide a bra that eases the pain and discomfort of breast engorgement or other conditions without the side effects associated with pharmacological treatments. It is a further object of the present invention to provide a bra that eases such discomfort while being usable in all situations. Finally, it is an object of the present invention to provide a bra usable with other conditions or situations including, but not limited to, breast mastitis and sports activity.

To achieve these objectives in accordance with the present invention, the bra provides gentle, adjustable compression and support of the breasts thereby relieving the pain and discomfort associated with breast engorgement. The bra allows the wearer to select the level of compression that best suits her needs and allows her to selectively incorporate warmth or coolness, as would be accomplished with baths and ice packs, with the adjustable compression. Further, the bra substantially and individually envelops the breasts providing additional relief from discomfort. Thus, the bra according to the present invention eases the pain associated with breast engorgement without the side effects associated with lactation suppressing drugs or the inconvenience of baths and ice packs.

In accordance with the present invention, a front panel and a back panel are provided and joined at the sides thereby forming a garment. Two connecting members are disposed in the garment and positioned to be opposable and selectively connectable. The two connectors can be connected at various positions thereby allowing variation in the girth of the bra. This feature provides adjustable compression of the breasts.

In the preferred embodiment of the present invention, the front and back panels are fabricated from a two layer material. Both layers are resilient and thus provide compression and envelopment of the breasts. The front panel is separated centrally and has cooperating connectors attached to each side of the front panel forming the separation. Preferably, the connectors are fashioned from velcro, registered trademark of Velcro Corporation relating to fastening devices incorporating loops of fabric on one strip of material and hooked fibers carried by another strip of material. Both velcro connectors are sufficiently wide to allow the connectors to be connected at various positions thereby affording adjustable compression. Connected between top portions of the front and back panels are straps that provide additional support of the breasts. Connected to the lower edge of the garment formed by the front and back panels is a support. The support is a narrow strip of material that also includes velcro connectors that are connectable at various positions. This variable connection in the support allows the support member to be sized to the girth of the wearer. Finally, in the preferred embodiment, the present invention includes a specific compress set which may be heated, cooled or frozen before placement against the inside surface of the front panel which can support the warm or cold compresses.

Other objects, features, and characteristics of the present invention as well as the methods of use of related elements will become more apparent upon consideration of the following description and the appended claims with reference to the accompanying drawings, wherein like reference numbers designate corresponding elements in the various figures.

DETAILED DESCRIPTION OF THE PRESENTLY PREFERRED EMBODIMENT

Figure 1:
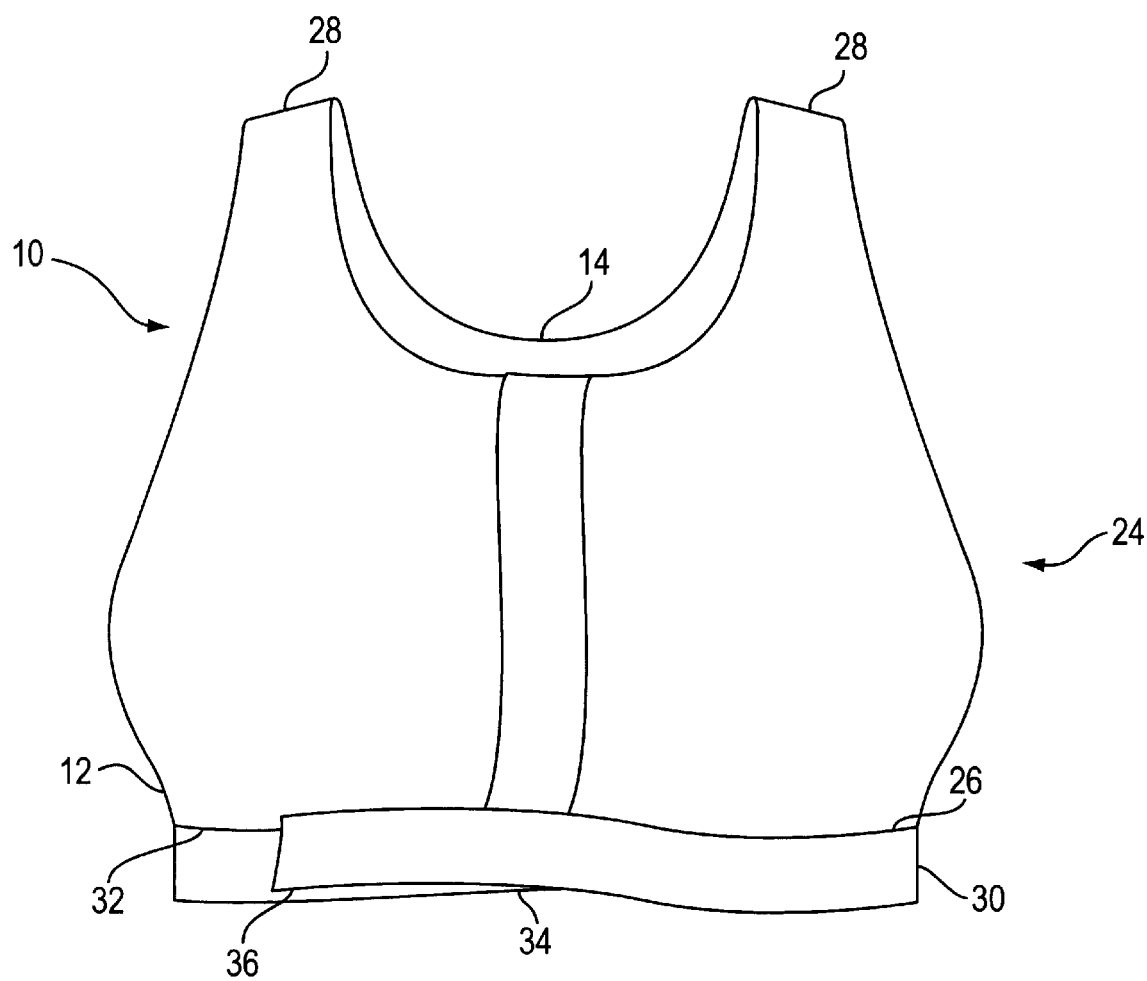
FIG. 1 is a front elevational view of a breast engorgement bra in accordance with the present invention.
Figure 2:
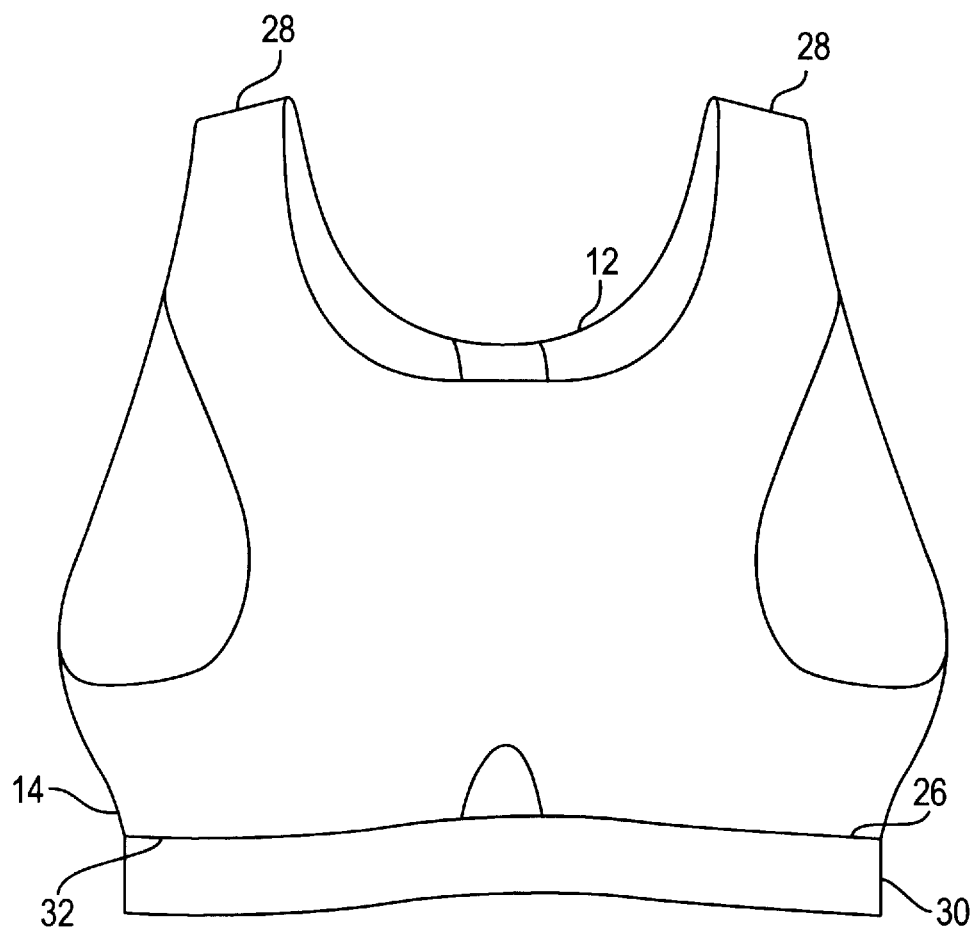
FIG. 2 is a rear elevational view of a breast engorgement bra in accordance with the present invention.

As shown in FIG. 1, a preferred embodiment of a breast engorgement bra in accordance with the present invention is designated generally by the reference number 10. A front panel 12 is provided. A back panel 14 is connected to portions of the front panel 12 thereby forming a garment 24 having a lower edge 26. The garment thus forms the main element of the breast engorgement bra. While the preferred embodiment of the present invention includes front and back panels, one skilled in the art will recognize readily that the garment 24 may also be fabricated from a single loop of material. As shown further in FIGS. 1 and 2, straps 28 are provided. End portions of the straps 28 are connected to top edges of the garment 24. Thus, each of the straps 28 are positioned generally parallel to each other and run generally fore and aft in reference to a wearer of the bra. While straps 28 are considered preferable, the broadest concept of the breast engorgement bra does not necessarily include straps.

Figure 3:
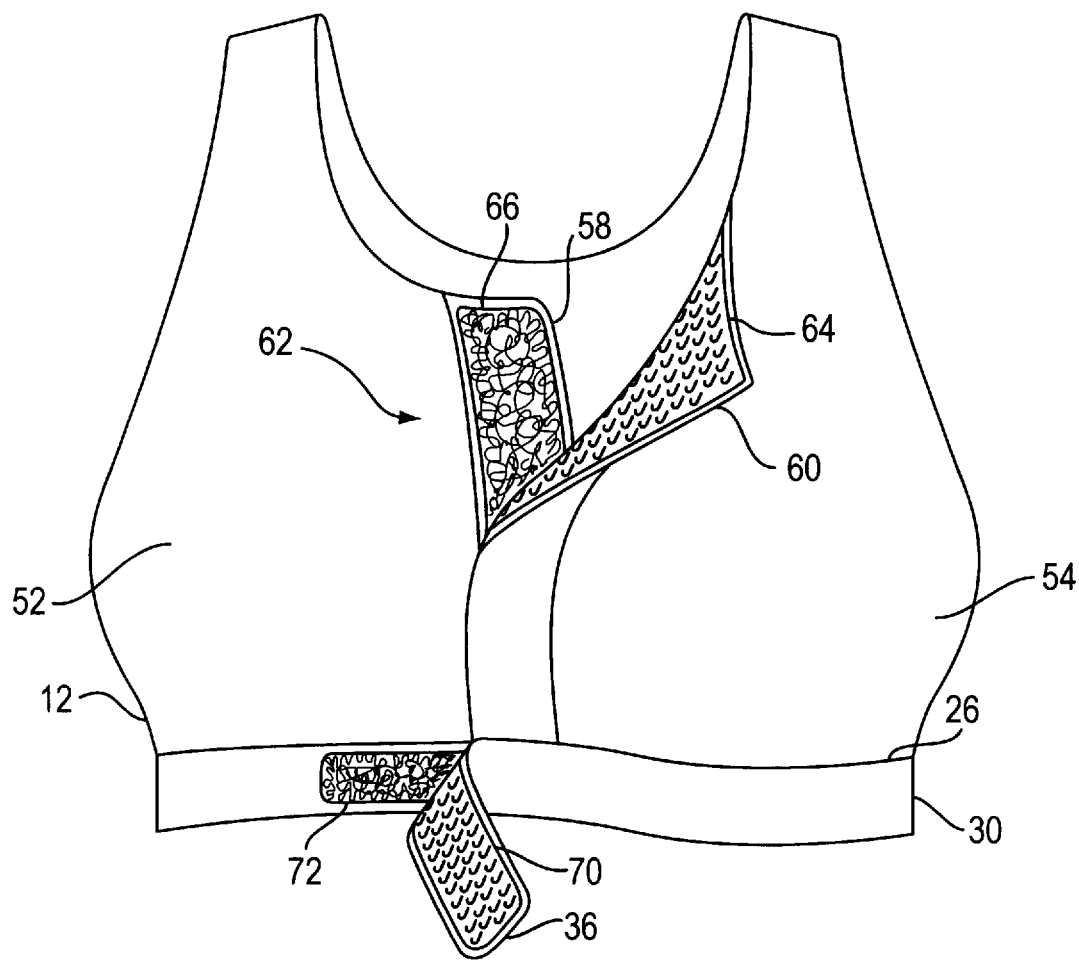
FIG. 3 is a perspective view of a breast engorgement bra in accordance with the present invention showing connecting members in a partially unconnected position.

The breast engorgement bra, as presently preferred, also includes a support 30 positioned below and connected to the lower edge 26 of the garment 24. The support 30 may have an annular configuration. Preferably, as described below, the support member 30 has a separation. In the preferred embodiment, a support top edge 32 of the support 30 is connected continuously to the garment 24 along the lower edge 26. When the breast engorgement bra is worn, the support 30 is positioned below the breasts of the wearer. As shown in FIG. 3, the support 30 includes both a support left end 34 and a support right end 36 of which both have connecting members attached. Those connecting members are described in more detail below. Notably, in the preferred embodiment of FIGS. 1–3, the support 30 is longer than a girth of the garment 24. Similarly, while the support member 30 is considered preferable, the broadest concept of the invention does not necessarily include the support 30.

As stated above, an object of the present invention is to provide adjustable compression of the breasts of the wearer of the breast engorgement bra. In light of that object, various structure of the breast engorgement bra is provided. First, the material and arrangement of the front panel 12 provides compression. Second, the connectors, as described below, provide adjustable compression.

Figure 4:
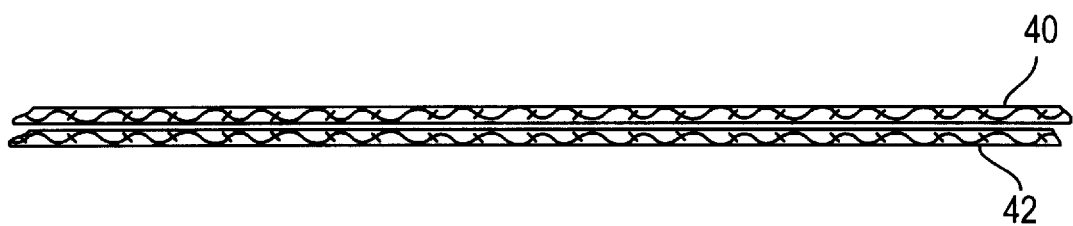
FIG. 4 is a sectional view of the material of the bra of FIG. 1.

In the preferred embodiment, the front panel 12 and/or the back panel 14 are fabricated from two layers of elastic or resilient material as shown in FIG. 4. An outside layer 40 is fabricated from irradiated, that is, head-set filament fibers having biaxial resiliency. Such a fabric provides the feel of natural fibers like cotton while also providing the strength of nylon. An inside layer 42 is fabricated from single filament, open-woven fibers also having biaxial resiliency. Such a fabric affords a comfortable interface between the wearer of the breast engorgement bra and the outside layer 40 while also providing support of the breasts.

As shown in FIG. 3, disposed within the front panel 12 are a left enveloping cup 52 and a right enveloping cup 54. Those cups are spaced laterally from each other along a perimeter of the lower edge of the garment 24. The left enveloping cup 52 is positioned adjacent to a left side of the front panel 12, and the right enveloping cup 54 is positioned adjacent to a right side of the front panel 12. When the breast engorgement bra 10 is worn, the right enveloping cup 54 and the left enveloping cup 52 envelop individually and substantially the breasts of the wearer providing encapsulating compression of the breasts. One skilled in the art will recognize readily that the broadest concept of the invention need not include enveloping cups. Centrally between the left enveloping cup 52 and the right enveloping cup 54, a separation in the garment 24 is formed between a left garment side 58 and a right garment side 60. The separation allows easier dressing and disrobing of the breast engorgement bra 10. While a separation is provided in the preferred embodiment, the broadest concept of the present invention need not include a separation.

As shown in FIG. 3, a compressing member 62 is disposed preferably in the garment 24 at the separation. The compressing member 62 includes a first connecting member 64 attached to the right garment side 60 and a second connecting member 66 attached to the left garment side 58. As one skilled in the art will recognize readily, the compressing member 62 need not be disposed in the garment 24 at the separation. For ease of use, however, the first connecting member 64 and the second connecting member 66 are opposable conveniently when attached to the right garment side 60 and the left garment side 58. To provide adjustable compression, both the first connecting member 64 and the second connecting member 66 have a width along the perimeter of the lower edge 26. The first connecting member 64 and the second connecting member 66 are connectable selectively at various positions along the width thereby changing the girth of the garment 24. In the preferred embodiment, the first connecting member 64 and the second connecting member 66 are fabricated from Velcro.

As shown in FIG. 3, the support 30 further includes a third connecting member 70 attached to the support right end 36 and a fourth connecting member 72 attached to the support left end 34. In this preferred embodiment, a separation in the support 30 is provided between the support right end 36 and the support left end 34 such that the separation in the support 30 is positioned below the separation in the garment 24. As explained above, the support right end 36 overlaps the support left end 34 and extends past the right garment side 60. As constructed, the third connecting member 70 and fourth connecting member 72 are opposable and can be attached selectively to various positions to encompass a girth of the wearer of the breast engorgement bra 10. In the preferred embodiment, the third connecting member 70 and the fourth connecting member 72 are fabricated from Velcro.

Figure 5:
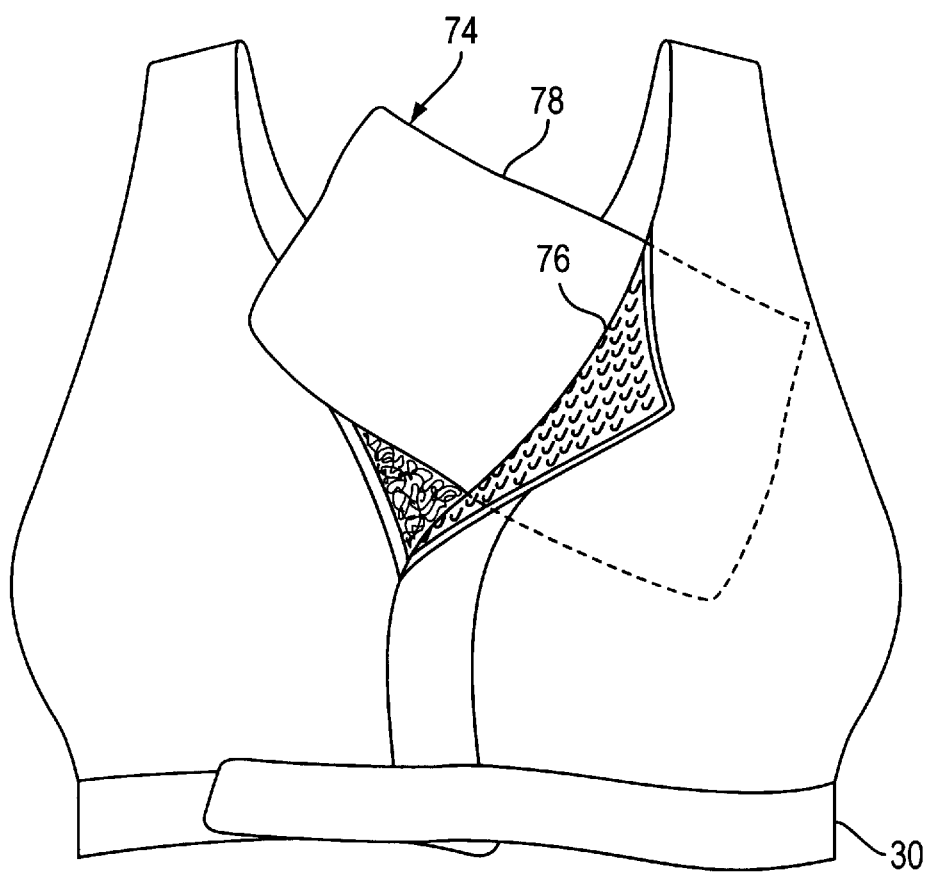
FIG. 5 is a perspective view of a warm or cold compress in combination with the bra of FIG. 1.
Figure 6:
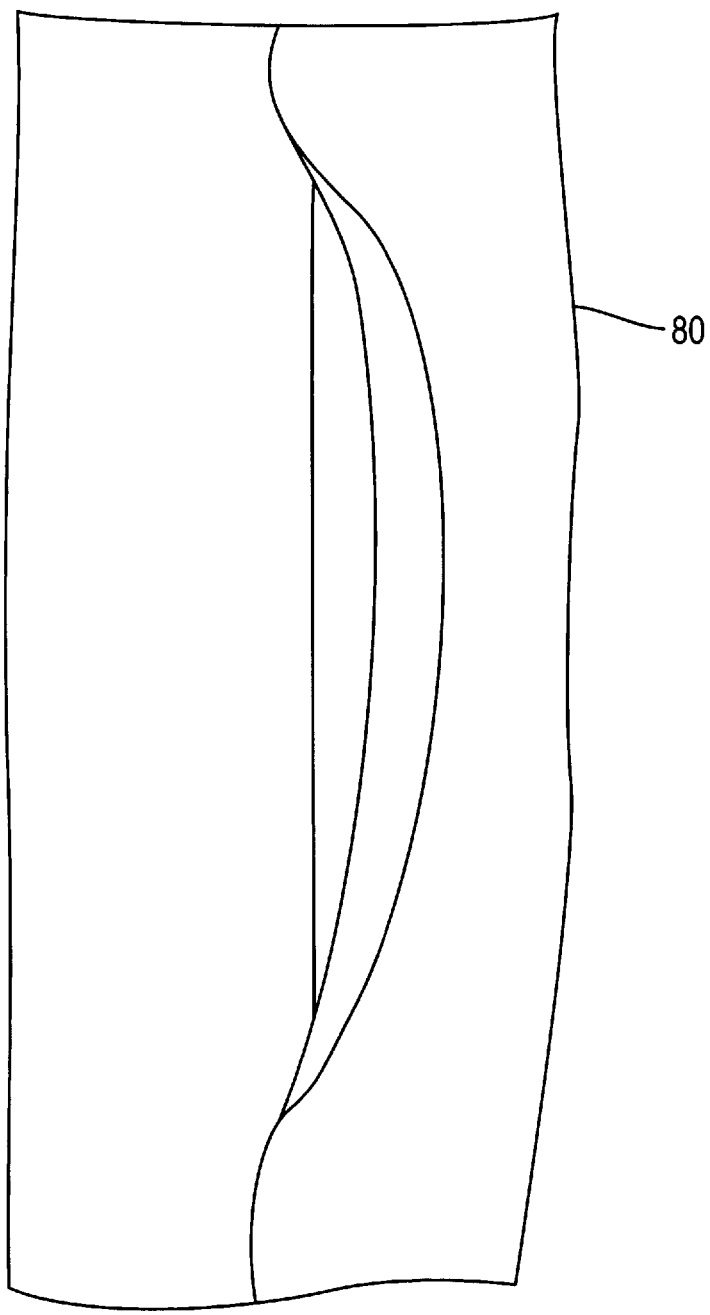
FIG. 6 is a perspective view of a covering for the warm or cold compress of FIG. 5.

To further ease the discomfort of breast engorgement, the present invention provides cold and warm compresses in combination with the bra. The cold compress is conformable to a shape of the body of a wearer of the bra even when frozen. As shown in FIG. 5, either a warming member or a cooling member 74 is supported removably by an inside surface 76 of the front panel 12. The warming member and the cooling member 74 include a shell 78 that contains a warming and cooling solution, respectively. In the present embodiment, the warming solution is the same as the cooling solution. Thus, the cooling member can function as both the cooling member and the warming member, and vice versa. Preferably, such a solution includes 85% water and 15% glycol. With that composition, the cooling member 74 is conformable to the shape of a body of the wearer even when frozen. As shown in FIG. 6, the warming member or the cooling member 74 may be inserted into an opening in a cotton covering 80 at the discretion of the user. As one skilled in the art will recognize readily, in the broadest concept of the invention, the warming member or the cooling member 74 may be used with traditional bras, or the breast engorgement bra 10 may be used without warm or cold compresses. In the preferred embodiment of the present invention, the warming-member or the cooling member 74 is used in combination with the breast engorgement bra 10. The preferred operation of the breast engorgement bra 10 will now be described. The wearer places the breast engorgement bra 10 on their body such that the back panel 14 contacts the wearer's back and the straps 28 are draped over the wearer's shoulders. The third connecting member 70 and the fourth connecting member 72 of the support 30 are connected such that the support 30 encompasses comfortably the girth of the wearer and is positioned immediately below the breasts. Thereafter, the first connecting member 64 is pulled into an opposed position near the second connecting member 66 and connected to the second connecting member 66 such that a desired level of compression is achieved. The first connecting member 64 and the second connecting member 66 can be repositioned to change the level of compression at the discretion of the wearer. As a consequence of the attachment of the first connecting member 64 to the second connecting member 66, the breasts are enveloped substantially by the left enveloping cup 52 and the right enveloping cup 54 thereby providing individual, encapsulating compression of the breasts.

If cold compression is desired, cooling members 74 are placed in a freezer, for example, until the cooling members 74 reach a desired temperature. Thereafter, the cooling members 74 are positioned between the breasts and the inside surface 76 of the front panel 12 and conformed to the shape of the body of the wearer such that the cooling members 74 are positioned on each breast from a position under an arm of the wearer towards a position at the center of the chest of the wearer thereby covering the top of each breast. Similarly, if warm compression is desired, warming members are placed in hot water or a microwave oven, for example, until the warming members reach a desired temperature. Thereafter, the warming members are positioned between the breasts and the inside surface 76 of the front panel 12 and conformed to the shape of the body of the wearer such that the warming members are positioned in the same manner as the cooling members 74.

While the invention has been described in connection with the preferred embodiment, it should be understood readily that the present invention is not limited to the disclosed embodiment. Rather, the present invention is intended to cover various equivalent arrangements including, for example, a breast engorgement bra and other arrangements included within the scope of the appended claims.

What is claimed is:

1. A bra supporting and compressing breasts comprising:
   a garment having a lower edge; and
   a compressing member disposed along the lower edge comprising
      a first connecting member attached to a first position along a perimeter of the lower edge,
      a second connecting member attached to a second position along the perimeter of the lower edge opposable to the first connecting member,
      the first connecting member being connectable to the second connecting member at a selectable position along the second connecting member such that a girth of the garment is selectively changeable thereby providing adjustable compression of the breasts,
   said bra including one of a cooling member and warming member in adjoining relationship with said bra, said member including a container enclosing a cooling and warming solution, said member being formable when frozen such that the member is conformable substantially to a shape of a body of the wearer of the bra, with said member being removably positionable inside said bra, said garment further comprising an inside layer and an outside layer in adjoining relationship with said inside layer, said bra further including a right end and a left end adjacent to the right end, the right end and the left end defining a separation in the support, a third connecting member attached to the right end, and a fourth connecting member attached to the left end opposable to the third connecting member, the third connecting member being selectively connectable to the fourth connecting member.

2. A bra according to claim 1, wherein the garment further comprises a back panel, and a front panel having portions connected to the back panel.

3. A bra according to claim 1, wherein the garment is fabricated from a resilient material.

4. A bra according to claim 1, wherein the garment is fabricated from an elastic material.

5. A bra according to claim 1, wherein the inside layer is fabricated from irradiated filament fibers, and the outside layer is fabricated from single filament, open-waved fibers.

6. A bra according to claim 1, wherein the garment further comprises a right enveloping cup disposed in the garment so as to substantially envelop a right breast when the bra is worn by a wearer, and a left enveloping cup disposed in the garment spaced laterally from the right enveloping cup so as to substantially envelop a left breast when the bra is worn by the wearer.

7. A bra according to claim 1, wherein the garment further comprises a left garment side disposed in the garment, a right garment side disposed in the garment and adjacent to the left garment side, the left garment side and the right garment side defining a separation in the garment.

8. A bra according to claim 7, wherein the first connecting member is attached to the right garment side, and the second connecting member is attached to the left garment side.

9. A bra according to claim 1, wherein one of the cooling member and the warming member further comprises a covering having an opening.

10. The bra as claimed in claim 1, wherein the container further comprises a shell for said cooling and warming solution which is confined by the shell, the cooling and warming solution comprising a solution of 85% water and 15% glycol.

* * * * *